(12) United States Patent
Liu et al.

(10) Patent No.: US 10,210,878 B2
(45) Date of Patent: Feb. 19, 2019

(54) METHOD AND SYSTEM FOR MATCHING MUSIC FILES WITH ELECTROENCEPHALOGRAM

(71) Applicant: Gold_NOAH (Beijing) Technology Co., Ltd., Shaanxi (CN)

(72) Inventors: Dongdong Liu, Beijing (CN); Bo Zhang, Beijing (CN); Xiaowen Yang, Beijing (CN)

(73) Assignee: Gold_NOAH (Beijing) Technology Co., Ltd., Shaanxi (CN)

( * ) Notice: Subject to any disclaimer, the term of this patent is extended or adjusted under 35 U.S.C. 154(b) by 397 days.

(21) Appl. No.: 14/957,415

(22) Filed: Dec. 2, 2015

(65) Prior Publication Data

US 2016/0086612 A1    Mar. 24, 2016

Related U.S. Application Data

(63) Continuation of application No. PCT/CN2014/086917, filed on Sep. 19, 2014.

(30) Foreign Application Priority Data

Jul. 25, 2014    (CN) .......................... 2014 1 0360309

(51) Int. Cl.
*G10L 19/022*    (2013.01)
*G06F 17/30*    (2006.01)
(Continued)

(52) U.S. Cl.
CPC .......... *G10L 19/022* (2013.01); *A61B 5/0482* (2013.01); *A61B 5/165* (2013.01);
(Continued)

(58) Field of Classification Search
None
See application file for complete search history.

(56) References Cited

U.S. PATENT DOCUMENTS 9,320,450 B2 *    4/2016    Badower .............. A61B 5/0476
2008/0140716 A1    6/2008    Saito et al.

FOREIGN PATENT DOCUMENTS

CN    101259015    6/2008
CN    102446533    5/2012
(Continued)

OTHER PUBLICATIONS

International Search Report dated Mar. 24, 2015 from PCT Application No. PCT/CN2014/086917.

*Primary Examiner* — Tuan-Khanh Phan
(74) *Attorney, Agent, or Firm* — Beyer Law Group LLP (57) ABSTRACT

Disclosed are a method and a system for matching an electroencephalogram and music files which compares the scaling index α of an electroencephalogram with the long-range correlation index β, and matches music file with the electroencephalogram if the scaling index and the long-range correlation index close to equal so as to find a music file matched with a measured electroencephalogram automatically. The method and system in accordance with the present invention may automatically find music files matching with human brain statements in real time by measuring an electroencephalogram, and then guide people relieve stress and relax effectively.

10 Claims, 2 Drawing Sheets

(51) Int. Cl.
*G10L 25/06* (2013.01)
*G10L 25/66* (2013.01)
*G10L 25/54* (2013.01)
*A61B 5/0482* (2006.01)
*A61B 5/16* (2006.01)

(52) U.S. Cl.
CPC ........ *G06F 17/30778* (2013.01); *G10L 25/06* (2013.01); *G10L 25/54* (2013.01); *G10L 25/66* (2013.01)

(56) References Cited

FOREIGN PATENT DOCUMENTS

| | | | | |
|---|---|---|---|---|
| CN | 102446533 A | * | 5/2012 | ............ G11B 27/10 |
| CN | 103412646 | | 11/2013 | |
| KR | 20080111972 | | 12/2008 | |

* cited by examiner

METHOD AND SYSTEM FOR MATCHING MUSIC FILES WITH ELECTROENCEPHALOGRAM

CLAIM OF PRIORITY AND CROSS-REFERENCE TO RELATED APPLICATION(S)

This application is a continuation of International Application No. PCT/CN2014/086917, filed Sep. 19, 2014. The International Application claims priority to Chinese Patent Application No. 201410360309.1, filed on Jul. 25, 2014. The afore-mentioned patent applications are hereby incorporated by reference in their entireties.

BACKGROUND OF THE INVENTION

1. Field of the Invention

The present invention relates to the field of neurotechnology, and particularly to a method and a system for matching music files with an electroencephalogram.

2. Description of the Related Art

There are numerous symbol sequences with abundant information in the natural world, such as human languages created by human, sound tone (e.g. music) and noises defined by human, and gene sequences and neural signaling forming in natural processes. Different kinds of sequences may be matched to each other according to some common elements.

Music is one of the artistic forms which express human emotions in a most direct way, and has a very important influence and promotion impact on human emotions and its transformation. The research on mechanism in human brain concerning with emotional response caused by music is becoming one of the hotspots in many fields such as the cognitive neuroscience, pedagogy and psychology. As verified by prior researches, music can affect human's emotions, which could be observed by electroencephalogram analysis. Furthermore, different types of music and different stimulations methods could cause different excitement modes on human brains. Therefore, how these lead to emotions, and further guide the music chosen to relieve stress and get relax become very important for clinic.

For now researches concentrate on different influences on human brains caused by different types of music. However, the major disadvantage of prior art is selecting music roughly and subjectively. More specifically, prior art is not able to automatically select music files to help people achieve a desired brain statement such as relax according to their real-time brain waves.

BRIEF DESCRIPTION OF THE INVENTION

The technical problem to be solved by the present invention is that prior art is not able to automatically find music files matching with human brain statements in real time then guide people relieve stress and relax effectively.

In view of this, in the first aspect, the present invention provides a method for matching music files with an electroencephalogram. In step S1, a scaling index α is obtained in accordance with a measured electroencephalogram. In step S2, each music file in a preset music library is analyzed to obtain a long-range correlation index β. In step S3, a music file matching with the electroencephalogram is searched out in accordance with the comparison of scaling index α and the long-range correlation index β.

Preferably, the step S1 may comprise following steps.

In step S11, the measured electroencephalogram is digitized to obtain a discrete-time signal sequence $\{x_i, i=1, 2, \ldots, N\}$, wherein $x_i$ is the ith sampling point of the electroencephalogram and N is the sampling size.

In step S12, the average amplitude $\langle x \rangle$ of the discrete-time signal sequence $\{x_i, i=1, 2, \ldots, N\}$ is filtered to obtain a sequence $\{y_i, i=1, 2, \ldots, N\}$, wherein $y_i$ is defined by the following formula.

$$y_i = \sum_{k=1}^{i}(x_k - \langle x \rangle), i = 1 \ldots N,$$

wherein, $$\langle x \rangle = \frac{1}{N}\sum_{i=1}^{N} x_i.$$

In step S13, the EMD (Empirical Mode Decomposition) is applied to the sequence $\{y_i, i=1, 2, \ldots, N\}$ to obtain n intrinsic mode functions IMF and a remainder R, wherein n is a positive integer determined by the EMD.

In step S14, peak-peak intervals (the number of data points between each neighboring local maximum) in each intrinsic mode function IMF are calculated.

In step S15, waveforms between peaks with peak-peak intervals within a first given range S are merged into a new waveform $Pvalue_s(k)$, wherein $10^{(m-1)} \leq s \leq 10^m$, $m=1, 2, \ldots, m_{max}$, and $m_{max}$ is determined by the length N of the sequence $\{y_i, i=1, 2, \ldots, N\}$, and k represents each data point of the merged waveform, wherein $k=1, 2, \ldots, k_{max}$, and $k_{max}$ is determined by the sum of all the peak-peak intervals within the first given range S.

In step S16, a root mean square of each merged waveform is calculated to obtain a wave function F.

$$F = \left[\frac{1}{Q}\sum_{k=1}^{Q} Pvalue_s^2(k)\right]^{1/2}$$

Wherein, $$Q = \frac{k_{max}}{\langle s \rangle},$$

and <S> represents calculating an average in range S. With respect to different scale ranges S, $F \propto s^\alpha$, wherein ∝ represents a directly proportional or scale relation between two subjects, and α is the scaling index.

In step S17, scaling index α is obtained in accordance with $F \propto s^\alpha$.

Preferably, the step S2 further comprises following steps.

In step S21, each music file in the music library is digitized to obtain a digital music signal sequence $\{U_i, i=1, 2, \ldots, M\}$, wherein i is the ith time point of the digital music signal sequence, and M is the length of the digital music signal sequence.

In step S22, a sequence $\{v_j, j=1, 2, \ldots, M/(presetlength)\}$ is obtained by dividing the digital music signal sequence $\{U_i, i=1, 2, \ldots, M\}$ into multiple sub-sequences with a preset length and calculating the standard deviation of each sub-sequence, wherein $v_j$ is the jth data of the sequence $\{v_j, j=1, 2, \ldots, M/(presetlength)\}$.

In step S23, an average intensity sequence $\{(v_j)^2, j=1, 2, \ldots, M/(presetlength)\}$ is obtained in accordance with the sequence $\{v_j, j=1, 2, \ldots, M/(presetlength)\}$.

In step S24, a fluctuation sequence $\{z_b, b=1, 2, \ldots, M/(presetlength)\}$ which is a one-dimensional random walk sequence is obtained in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula.

$$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2.$$

In step S25, multiple sub-sequences are obtained by shifting a time window with preset width along the fluctuation sequence $\{z_b, b=1, 2, \ldots, M/(presetlength)\}$. Each two neighboring windows exist a fixed overlap length $\tau$.

In step S26, a linear trend $\hat{z}_b$ of each sub-sequence is obtained by mean of linear regression.

In step S27, a detrended fluctuation function $F_D(presetwidth) = \sqrt{\langle(\delta z)^2\rangle}$ is obtained in accordance with the sequence $\{z_b, b=1, 2, \ldots, M/(presetlength)\}$ and the linear trend of each sub-sequence, wherein $\delta z = \hat{z}_b - z_b$, and $\sqrt{\langle(\delta z)^2\rangle}$ represents calculating the average of $(\delta z)^2$ in each time window.

In step S28, the long-range correlation index $\beta$ is obtained in accordance with the detrended fluctuation function $F_D(presetwidth)$ by means of following formula:

$$\beta = \frac{d\log F_D(presetwidth)}{d\log(presewidth+3)},$$

wherein, $$\frac{d\log F_D(presetwidth)}{d\log(presewidth+3)}$$

represents the relation between detrended fluctuation function and the time scaling defined by the preset width of the time window derived from log-log plot.

Preferably, the step S3 further comprises following steps.

In step S31, $\gamma$ is calculated in accordance with the scaling index $\alpha$ and the long-range correlation index $\beta$, wherein, $\gamma = |\alpha - \beta|$.

In step S32, if $\gamma$ is within a second given range, the music file with a long-range correlation index $\beta$ is matched with the electroencephalogram with a scaling index $\alpha$.

In a second aspect, the present invention provides a system for matching music files with an electroencephalogram which comprises an electroencephalogram scaling device, a music analysis device and a matching device. The electroencephalogram scaling device is configured to obtain a scaling index $\alpha$ in accordance with a measured electroencephalogram and to transmit the scaling index $\alpha$ to the matching device. The music analysis device is configured to analyze each music file in a preset music library to obtain a long-range correlation index $\beta$ and to transmit $\beta$ to the matching device. The matching device is configured to search out a music file matching with the electroencephalogram in accordance with the comparison of the scaling index $\alpha$ and the long-range correlation index $\beta$.

The system further comprises an electroencephalogram measuring device configured to measure an electroencephalogram and to transmit the electroencephalogram to the electroencephalogram scaling device.

Preferably, the electroencephalogram scaling device is configured to implement following steps.

In step S11, the measured electroencephalogram is digitized to obtain a discrete-time signal sequence $\{x_i, i=1, 2, \ldots, N\}$, wherein $x_i$ is the ith sampling point of the electroencephalogram and N is the sampling size.

In step S12, the average amplitude $\langle x \rangle$ of the discrete-time signal sequence $\{x_i, i=1, 2, \ldots, N\}$ is filtered to obtain a sequence $\{y_i, i=1, 2, \ldots, N\}$, wherein $y_i$ is defined by the following formula.

$$y_i = \sum_{k=1}^{i} (x_k - \langle x \rangle), i = 1 \ldots N,$$

wherein, $$\langle x \rangle = \frac{1}{N} \sum_{i=1}^{N} x_i.$$

In step S13, the EMD (Empirical Mode Decomposition) is applied to the sequence $\{y_i, i=1, 2, \ldots, N\}$ to obtain n intrinsic mode functions IMF and a remainder R, wherein n is a positive integer determined by the EMD.

In step S14, peak-peak intervals (the number of data points between each neighboring local maximum) in each intrinsic mode function IMF are calculated.

In step S15, waveforms between peaks with peak-peak intervals within a first given range S are merged into a new waveform $Pvalue_s(k)$, wherein $10^{(m-1)} \leq s \leq 10^m$, $m=1, 2, \ldots, m_{max}$, and $m_{max}$ is determined by the length N of the sequence $\{y_i, i=1, 2, \ldots, N\}$, and k represents each data point of the merged waveform, wherein $k=1, 2, \ldots, k_{max}$, and $k_{max}$ is determined by the sum of all the peak-peak intervals within the first given range S.

In step S16, root mean square of each merged waveform is calculated to obtain a wave function F.

$$F = \left[\frac{1}{Q} \sum_{k=1}^{Q} Pvalue_s^2(k)\right]^{1/2},$$

wherein, $$Q = \frac{k_{max}}{\langle s \rangle},$$

and <S> represents calculating an average in the given range S. With respect to different scale ranges S, F∝s$^\alpha$, wherein ∝ represents a directly proportional or scale relation between two subjects, and α is the scaling index.

In step S17, scaling index α is obtained in accordance with F∝s$^\alpha$.

Preferably, the music analysis device is configured to implement following steps.

In step S21, each music file in the music library is digitized to obtain a digital music signal sequence $\{U_i, i=1, 2, \ldots, M\}$, wherein i is the ith time point of the digital music signal sequence, and M is the length of the digital music signal sequence.

In step S22, a sequence $\{v_j, j=1, 2, \ldots, M/(presetlength)\}$ is obtained by dividing the digital music signal sequence $\{U_i, i=1, 2, \ldots, M\}$ into multiple sub-sequences with a preset length and calculating the standard deviation of each sub-sequence, wherein $v_j$ is the jth data of the sequence $\{v_j, j=1, 2, \ldots, M/(presetlength)\}$.

In step S23, an average intensity sequence $\{(v_j)^2, j=1, 2, \ldots, M/(presetlength)\}$ is obtained in accordance with the sequence $\{v_j, j=1, 2, \ldots, M/(presetlength)\}$.

In step S24, a fluctuation sequence $\{z_b, b=1, 2, \ldots, M/(presetlength)\}$ which is a one-dimensional random walk sequence is obtained in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula.

$$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2.$$

In step S25, multiple sub-sequences are obtained by shifting a time window with preset width along the fluctuation sequence $\{z_b, b=1, 2, \ldots, M/(presetlength)\}$ $\{z_b, b=1, 2, \ldots, M/(presetlength)\}$. Each two neighboring windows exist a fixed overlap length τ.

In step S26, a linear trend $\hat{z}_b$ of each sub-sequence is obtained by mean of linear regression.

In step S27, a detrended fluctuation function $F_D$(presetwidth)=$\sqrt{\langle(\delta z)^2\rangle}$ is obtained in accordance with the sequence $\{z_b, b=1, 2, \ldots, M/(presetlength)\}$ and the linear trend of each sub-sequence, wherein $\delta z = z_b - \hat{z}_b$, and $\langle(\delta z)^2\rangle$ represents calculating the average of $(\delta z)^2$ in each time window.

In step S28, the long-range correlation index β is obtained in accordance with the detrended fluctuation function $F_D$(presetwidth) by means of following formula:

$$\beta = \frac{d\log F_D(presetwidth)}{d\log(presewidth + 3)},$$

wherein, $$\frac{d\log F_D(presetwidth)}{d\log(presewidth + 3)}$$

represents the relation between detrended fluctuation function and the time scaling defined by the preset width of the time window derived from log-log plot.

Preferably, the matching device is configured to implement following steps.

In step S31, γ is calculated in accordance with the scaling index α and the long-range correlation index β, wherein, γ=|α−β|.

In step S32, if γ is within a second given range, the music file with a long-range correlation index β is matched with the electroencephalogram with a scaling index α.

1. Advantageous Effects

The method and system for matching music files with an electroencephalogram in accordance with the present invention may select corresponding music files in accordance with different electroencephalogram. In other words, the method and system in accordance with the present invention may automatically find music files matching with human brain statements in real time then guide people relieve stress and relax effectively.

DETAILED DESCRIPTION OF EMBODIMENTS OF THE INVENTION

For better understanding to the objects, subject matter and advantages of the embodiments in accordance with the present invention, reference will now be made in detail to particular embodiments of the disclosure, examples of which are illustrated in the accompanying drawings. Obviously, the embodiments to be introduced below should not be construed to be restrictive to the scope, but illustrative only. Those skilled in the art would understand that other embodiments obtained in accordance with the spirit of the present invention without exercising inventive skills also fall into the scope of the present invention.

The First Embodiment

Figure 1:
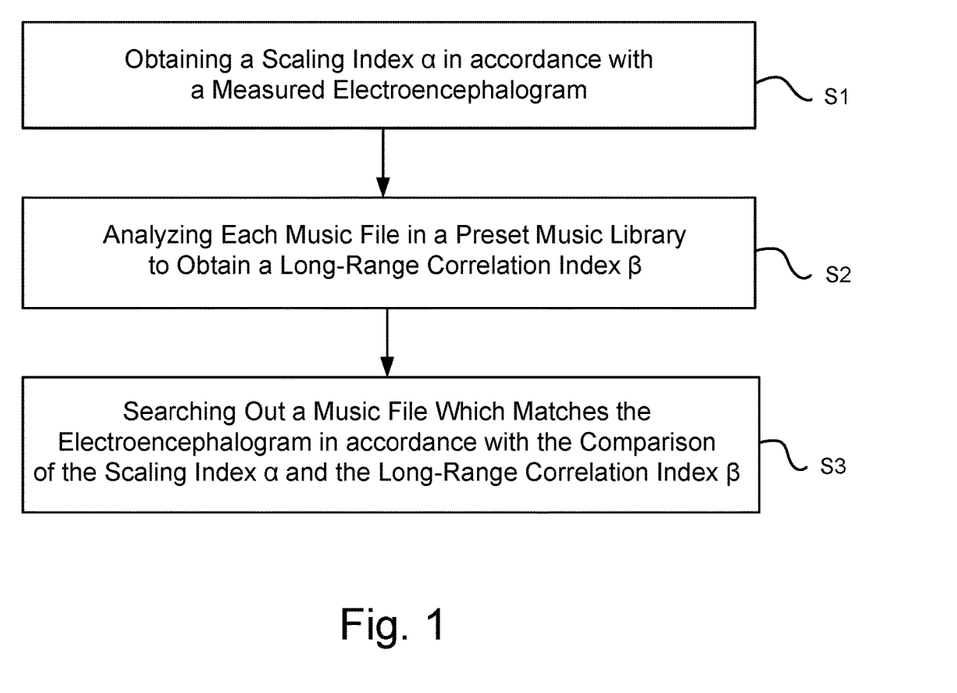
FIG. 1 is a flow chart of the method for matching an electroencephalogram and music files in accordance with a first embodiment.
Figure 2:
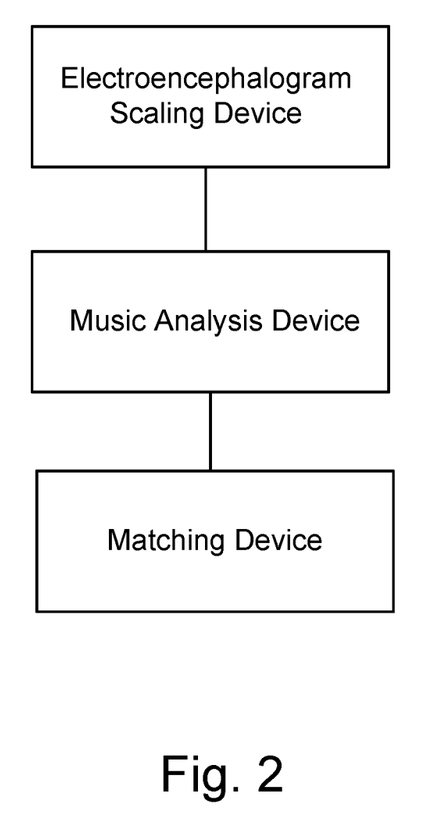
FIG. 2 is a diagram of the system for matching an electroencephalogram and music files in accordance with a second embodiment.

A method for matching music files with an electroencephalogram is disclosed by the present embodiment which comprises following steps as illustrated in FIG. 1.

In step S1, a scaling index α is obtained in accordance with a measured electroencephalogram. In step S2, each music file in a preset music library is analyzed to obtain a long-range correlation index β. In step S3, a music file matching with the electroencephalogram is searched out in accordance with the comparison of the scaling index α and the long-range correlation index β.

Furthermore, the step S1 may comprise following steps which is not illustrated in FIG. 1.

In step S11, the measured electroencephalogram is digitized to obtain a discrete-time signal sequence $\{x_i, i=1, 2, \ldots, N\}$, wherein $x_i$ is the ith sampling point of the electroencephalogram and N is the sampling size.

In step S12, the average amplitude $\langle x \rangle$ of the discrete-time signal sequence $\{x_i, i=1, 2, \ldots, N\}$ is filtered to obtain a sequence $\{y_i, i=1, 2, \ldots, N\}$, wherein $y_i$ is defined by the following formula.

$$y_i = \sum_{k=1}^{i} (x_k - \langle x \rangle), i = 1 \ldots N,$$

wherein, $$\langle x \rangle = \frac{1}{N} \sum_{i=1}^{N} x_i.$$

In step S13, the EMD (Empirical Mode Decomposition) is applied to the sequence $\{y_i, i=1, 2, \ldots, N\}$ to obtain n intrinsic mode functions IMF and a remainder R, wherein n is a positive integer determined by the EMD.

In step S14, peak-peak intervals (the number of data points between each neighboring local maximum) in each intrinsic mode function IMF are calculated.

In step S15, waveforms between peaks with peak-peak intervals within a first given range S is merged into a new waveform $Pvalue_s(k)$, wherein $10^{(m-1)} \leq s \leq 10^m$, $m=1, 2, \ldots, m_{max}$, and $m_{max}$ is determined by the length N of the sequence $\{y_i, i=1, 2, \ldots, N\}$, and k represents each data point of the merged waveform, wherein $k=1, 2, \ldots, k_{max}$ and $k_{max}$ is determined by the sum of all the peak-peak intervals within the first preset range S.

In step S16, a root mean square of each merged waveform is calculated to obtain a wave function F.

$$F = \left[ \frac{1}{Q} \sum_{k=1}^{Q} Pvalue_s^2(k) \right]^{1/2},$$

wherein, $$Q = \frac{k_{max}}{\langle s \rangle},$$

and <S> represents calculating an average in range S. With respect to different scale ranges S, $F \propto s^\alpha$, wherein ∝ directly proportional or scale relation between two subjects, and α is the scaling index.

In step S17, scaling index α is obtained in accordance with $F \propto s^\alpha$.

Furthermore, the step S2 may comprise following steps which is not illustrated in FIG. 1.

In step S21, each music file in the music library is digitized to obtain a digital music signal sequence $\{U_i, i=1, 2, \ldots, M\}$, wherein i is the ith time point of the digital music signal sequence, and M is the length of the digital music signal sequence.

In step S22, a sequence $\{v_j, j=1, 2, \ldots, M/(presetlength)\}$ is obtained by dividing the digital music signal sequence $\{U_i, i=1, 2, \ldots, M\}$ into multiple sub-sequences with a preset length and calculating the standard deviation of each sub-sequence, wherein $v_j$ is the jth data of the sequence $\{v_j, j=1, 2, \ldots, M/(presetlength)\}$.

In step S23, an average intensity sequence $\{(v_j)^2, j=1, 2, \ldots, M/(presetlength)\}$ is obtained in accordance with the sequence $\{v_j, j=1, 2, \ldots, M/(presetlength)\}$.

In step S24, a fluctuation sequence $\{z_b, b=1, 2, \ldots, M/(presetlength)\}$ which is a one-dimensional random walk sequence is obtained in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula.

$$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2.$$

In step S25, multiple sub-sequences are obtained by shifting a time window with preset width along the fluctuation sequence $\{z_b, b=1, 2, \ldots, M/(presetlength)\}$. Each two neighboring windows exist a fixed overlap length τ.

In step S26, a linear trend $\hat{z}_b$ of each sub-sequence is obtained by mean of linear regression, wherein, $\hat{z}_b = a + cr$, and a and c are determined by linear regression, and the multiple sub-sequences correspond to multiple $\hat{z}_b$, a and c in each $\hat{z}_b = a + cr$ may be different.

In step S27, a detrended fluctuation function $F_D(presetwidth) = \sqrt{\langle (\delta z)^2 \rangle}$ is obtained in accordance with the sequence $\{z_b, b=1, 2, \ldots, M/(presetlength)\}$ and the linear trend of each sub-sequence, wherein $\delta z = z_b - \hat{z}_b$, and $\langle (\delta z)^2 \rangle$ represents calculating the average of $(\delta z)^2$ in each time window.

In step S28, the long-range correlation index β is obtained in accordance with the detrended fluctuation function $F_D(presetwidth)$ by means of following formula:

$$\beta = \frac{d \log F_D(presetwidth)}{d \log(presewidth + 3)},$$

wherein, $$\frac{d \log F_D(presetwidth)}{d \log(presewidth + 3)}$$

represents the relation between detrended fluctuation function and the time scaling defined by the preset width of the time window derived from log-log plot.

The step S3 may comprise following steps which is not illustrated in FIG. 1.

In step S31, γ is calculated in accordance with the scaling index α and the long-range correlation index β, wherein, γ=|α−β|.

In step S32, if γ is with a second given range, the music file with a long-range correlation index β is matched with the electroencephalogram with a scaling index α.

The method in accordance with the present embodiment compares the scaling index α of an electroencephalogram with the long-range correlation index β, and matches music file with the electroencephalogram if the scaling index and the long-range correlation index close to equal so as to find a music file matching with a measured electroencephalogram automatically. The method in accordance with the present embodiment may find music files match with human brain state automatically in real time by measuring an electroencephalogram then guide people relieve stress and relax effectively.

The Second Embodiment

A system for matching music files with an electroencephalogram is disclosed by the present embodiment which comprises an electroencephalogram scaling device, a music analysis device and a matching device as illustrated in FIG. 1.

The electroencephalogram scaling device is configured to obtain a scaling index α in accordance with a measured electroencephalogram and to transmit the scaling index α to the matching device. The music analysis device is configured to analyze each music file in a preset music library to obtain a long-range correlation index β and to transmit β to the matching device. The matching device is configured to search out a music file matching with the electroencephalogram in accordance with the comparison of the scaling index α and the long-range correlation index β.

The system further comprises an electroencephalogram measuring device not illustrated in FIG. 1. The electroencephalogram measuring device is configured to measure an electroencephalogram and to transmit the electroencephalogram to the electroencephalogram scaling device.

In a preferable embodiment, the electroencephalogram scaling device is configured to implement following steps.

In step S11, the measured electroencephalogram is digitized to obtain a discrete-time signal sequence $\{x_i, i=1, 2, \ldots, N\}$, wherein xi is the ith sampling point of the electroencephalogram and N is the sampling size.

In step S12, the average amplitude $\langle x \rangle$ of the discrete-time signal sequence $\{x_i, i=1, 2, \ldots, N\}$ is filtered to obtain a sequence $\{y_i, i=1, 2, \ldots, N\}$, wherein $y_i$ is defined by the following formula.

$$y_i = \sum_{k=1}^{i} (x_k - \langle x \rangle), i = 1 \ldots N,$$

wherein $$\langle x \rangle = \frac{1}{N} \sum_{i=1}^{N} x_i.$$

In step S13, the EMD (Empirical Mode Decomposition) is applied to the sequence $\{y_i, i=1, 2, \ldots, N\}$ to obtain n intrinsic mode functions IMF and a remainder R, wherein n is a positive integer determined by the EMD.

In step S14, peak-peak intervals (the number of data points between each neighboring local maximum) in each intrinsic mode function IMF are calculated.

In step S15, waveforms between peaks with peak-peak intervals with length within a first given range S are merged into a new waveform $Pvalue_s(k)$, wherein $10^{(m-1)} \le s \le 10^m$, $m=1, 2, \ldots, m_{max}$, and $m_{max}$ is determined by the length N of the sequence $\{y_i, i=1, 2, \ldots, N\}$, and k represents each data point of the merged waveform, wherein $k=1, 2, \ldots, k_{max}$ and $k_{max}$ is determined by the sum of all the peak-peak intervals within the first given range S.

In step S16, root mean square of each merged waveform is calculated to obtain a wave function F.

$$F = \left[ \frac{1}{Q} \sum_{k=1}^{Q} Pvalue_s^2(k) \right]^{1/2},$$

wherein, $$Q = \frac{k_{max}}{\langle s \rangle},$$

and <S> represents calculating an average in range S. With respect to different scale ranges S, $F \propto s^\alpha$, wherein ∝ represents a directly proportional or scale relation between two subjects, and α is the scaling index.

In step S17, scaling index α is obtained in accordance with $F \propto s^\alpha$.

More specifically, the music analysis device is configured to implement following steps.

In step S21, each music file in the music library is digitized to obtain a digital music signal sequence $\{U_i, i=1, 2, \ldots, M\}$, wherein i is the ith time point of the digital music signal sequence, and M is the length of the digital music signal sequence.

In step S22, a sequence $\{v_j, j=1, 2, \ldots, M/(presetlength)\}$ is obtained by dividing the digital music signal sequence $\{U_i, i=1, 2, \ldots, M\}$ into multiple sub-sequences with a preset length and calculating the standard deviation of each sub-sequence, wherein $v_j$ is the jth data of the sequence $\{v_j, j=1, 2, \ldots, M/(presetlength)\}$.

In step S23, an average intensity sequence $\{(v_j)^2, j=1, 2, \ldots, M/(presetlength)\}$ is obtained in accordance with the sequence $\{v_j, j=1, 2, \ldots, M/(presetlength)\}$.

In step S24, a fluctuation sequence $\{z_b, b=1, 2, \ldots, M/(presetlength)\}$ which is a one-dimensional random walk sequence is obtained in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula.

$$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2.$$

In step S25, multiple sub-sequences are obtained by shifting a time window with preset width along the fluctuation sequence $\{z_b, b=1, 2, \ldots, M/(presetlength)\}$. Each two neighboring windows exist a fixed overlap length $\tau$.

In step S26, a linear trend $\hat{z}_b$ of each sub-sequence is obtained by mean of linear regression.

In step S27, a detrended fluctuation function $F_D$(presetwidth)=$\sqrt{\langle(\delta z)^2\rangle}$ is obtained in accordance with the sequence $\{z_b, b=1, 2, \ldots, M/(presetlength)\}$ and the linear trend of each sub-sequence, wherein $\delta z = z_b - \hat{z}_b$, and $\langle(\delta z)^2\rangle$ represents calculating the average of $(\delta z)^2$ in each time window.

In step S28, the long-range correlation index $\beta$ is obtained in accordance with the detrended fluctuation function $F_D$(presetwidth) by means of following formula:

$$\beta = \frac{d\log F_D(presetwidth)}{d\log(presewidth+3)},$$

wherein, $$\frac{d\log F_D(presetwidth)}{d\log(presewidth+3)}$$

represents the relation between detrended fluctuation function and the time scaling defined by the preset width of the time window derived from log-log plot.

More specifically, the matching device is configured to implement following steps.

In step S31. $\gamma$ is calculated in accordance with the scaling index $\alpha$ and the long-range correlation index $\beta$, wherein, $\gamma=|\alpha-\beta|$.

In step S32, if $\gamma$ is within a second given range, the music file with a long-range correlation index $\beta$ is matched with the electroencephalogram with a scaling index $\alpha$.

The system in accordance with the present embodiment may automatically find music files matching with human brain statements in real time by measuring an electroencephalogram, and then guide people relieve stress and relax effectively.

While embodiments of this disclosure have been shown and described, it will be apparent to those skilled in the art that more modifications are possible without departing from the spirits herein. The disclosure, therefore, is not to be restricted except in the spirit of the following claims.

The method and system for matching music files with an electroencephalogram in accordance with the present invention may select corresponding music files in accordance with different electroencephalogram. In other words, the method and system in accordance with the present invention may automatically find music files matching with human brain statements in real time by measuring an electroencephalogram, and then guide people relieve stress and relax effectively.

We claim:
1. A computer-implemented method for matching music files with an electroencephalogram, comprising:
   obtaining a scaling index $\alpha$ in accordance with a measured electroencephalogram;
   analyzing each music file in a preset music library to obtain a long-range correlation index $\beta$;
   searching out a music file which matches the electroencephalogram in accordance with the comparison of the scaling index $\alpha$ and the long-range correlation index $\beta$; and
   playing, via a music player, the music file which matches the electroencephalogram,
   wherein said obtaining a scaling index $\alpha$ further comprises:
   digitizing said measured electroencephalogram to obtain a discrete-time signal sequence $\{x_i, i=1, 2, \ldots, N\}$, wherein $x_i$ is the ith sampling point of said electroencephalogram and N is the sampling size;
   filtering the average amplitude $\langle x \rangle$ from said discrete-time signal sequence $\{x_i, i=1, 2, \ldots, N\}$ to obtain a sequence $\{y_i, i=1, 2, \ldots, N\}$, wherein $y_i$ is defined by the following formula,

$$y_i = \sum_{k=1}^{i} (x_k - \langle x \rangle), i = 1 \ldots N,$$

wherein, $$\langle x \rangle = \frac{1}{N} \sum_{i=1}^{N} x_i;$$

applying an Empirical Mode Decomposition (EMD) to said sequence $\{y_i, i=1, 2, \ldots, N\}$ to obtain n intrinsic mode functions and a remainder, wherein n is a positive integer determined by said EMD;
calculating peak-peak intervals in each intrinsic mode function;
merging waveforms between peaks with peak-peak intervals within a first given range S into a new waveform Pvalue$_s$(k), wherein $10^{(m-1)} \leq s \leq 10^m$, $m=1, 2, \ldots, m_{max}$, and $m_{max}$ is determined by the length N of said sequence $\{y_i, i=1, 2, \ldots, N\}$, and k represents each data point of said merged waveform, wherein $k=1, 2, \ldots, k_{max}$, and $k_{max}$ is determined by the sum of all the peak-peak intervals within the first given range S;
calculating a root mean square of each merged waveform to obtain a wave function F, wherein, $$F = \left[\frac{1}{Q} \sum_{k=1}^{Q} Pvalue_s^2(k)\right]^{1/2},$$

wherein, $$Q = \frac{k_{max}}{\langle s \rangle},$$

and $\langle S \rangle$ represents calculating an average in range S, and with respect to different scale ranges S, $F \propto s^\alpha$, wherein ∝ represents a directly proportional or scale relation between two subjects, and α is the scaling index; and obtaining scaling index α in accordance with F∝s^α.

2. The method of claim 1, wherein, said analyzing each music file further comprises:

digitizing each music file in the music library to obtain a digital music signal sequence $\{U_i, i=1, 2, \ldots, M\}$, wherein i is the ith time point of said digital music signal sequence, and M is the length of said digital music signal sequence;

obtaining a sequence $\{v_j, j=1, 2, \ldots, M/(\text{presetlength})\}$ by dividing said digital music signal sequence $\{U_i, i=1, 2, \ldots, M\}$ into multiple sub-sequences with a preset length and calculating the standard deviation of each sub-sequence, wherein $v_j$ is the jth data of said sequence $\{v_j, j=1, 2, \ldots, M/(\text{presetlength})\}$;

obtaining an average intensity sequence in accordance with the sequence $\{v_j, j=1, 2, \ldots, M/(\text{presetlength})\}$;

obtaining a fluctuation sequence $\{z_b, b=1, 2, \ldots, M/(\text{presetlength})\}$ which is a one-dimensional random walk sequence in accordance with the average intensity sequence $\{(v_j)^2, j=1, 2, \ldots, M/(\text{presetlength})\}$, wherein $z_b$ is the bth data of the sequence $\{z_b, b=1, 2, \ldots, M/(\text{presetlength})\}$ which is defined by the following formula, $$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2;$$

obtaining multiple sub-sequences by shifting a time window with preset width along said fluctuation sequence $\{z_b, b=1, 2, \ldots, M/(\text{presetlength})\}$ with each two neighboring windows exist a fixed overlap length τ;

obtaining a linear trend $\hat{z}_b$ of each sub-sequence by mean of linear regression;

obtaining a detrended fluctuation function $F_D(\text{presetwidth})=\sqrt{\langle(\delta z)^2\rangle}$ in accordance with said sequence $\{z_b, b=1, 2, \ldots, M/(\text{presetlength})\}$ and said linear trend of each sub-sequence, wherein $\delta z = z_b - \hat{z}_b$, and $\langle(\delta z)^2\rangle$ represents calculating the average of $(\delta z)^2$ in the time window; and obtaining said long-range correlation index β in accordance with said detrended fluctuation function $F_D(\text{presetwidth})$ by means of following formula:

$$\beta = \frac{d\log F_D(presetwidth)}{d\log(presewidth+3)},$$

wherein, $$\frac{d\log F_D(presetwidth)}{d\log(presewidth+3)}$$

represents the relation between said detrended fluctuation function and the time scaling defined by said preset width of said time window derived from log-log plot.

3. The method of claim 1, wherein, said searching out a music file further comprises:

calculating γ in accordance with the scaling index α and the long-range correlation index β, wherein, γ=|α−β|; and if γ is within a second given range, the music file with said long-range correlation index β is matched with the electroencephalogram with said scaling index α.

4. A system for matching music files with an electroencephalogram, comprising:

a music player;

an electroencephalogram scaling device configured to obtain a scaling index α in accordance with a measured electroencephalogram and to transmit said scaling index α to a matching device;

a music analysis device configured to analyze each music file in a preset music library to obtain a long-range correlation index β and to transmit β to said matching device; and a matching device configured to search out a music file matching with the electroencephalogram in accordance with the comparison of the scaling index α and the long-range correlation index β and cause the music player to play the music file which matches the electroencephalogram, wherein said electroencephalogram scaling device is configured to implement following steps:

digitizing said measured electroencephalogram to obtain a discrete-time signal sequence $\{x_i, i=1, 2, \ldots, N\}$, wherein $x_i$ is the ith sampling point of said electroencephalogram and N is the sampling size;

filtering the average amplitude ⟨x⟩ from said discrete-time signal sequence $\{x_i, i=1, 2, \ldots, N\}$ to obtain a sequence $\{y_i, i=1, 2, \ldots, N\}$, wherein $y_i$ is defined by the following formula, $$y_i = \sum_{k=1}^{i} (x_k - \langle x \rangle), i = 1 \ldots N,$$

wherein $$\langle x \rangle = \frac{1}{N} \sum_{i=1}^{N} x_i;$$

applying an Empirical Mode Decomposition (EMD) to said sequence $\{y_i, i=1, 2, \ldots, N\}$ to obtain n intrinsic mode functions and a remainder, wherein n is a positive integer determined by said EMD;

calculating peak-peak intervals in each intrinsic mode function;

merging waveforms between peaks with peak-peak intervals within a first given range S into a new waveform $Pvalue_s(k)$, wherein $10^{(m-1)} \le s \le 10^m$, $m=1, 2, \ldots, m_{max}$, and $m_{max}$ is determined by the length N of said sequence, $\{y_i, i=1, 2, \ldots, N\}$, and k represents each data point of said merged waveform, wherein $k=1, 2, \ldots, k_{max}$, and $k_{max}$ is determined by the sum of all the peak-peak intervals within the first given range S;

calculating a root mean square of each merged waveform to obtain a wave function F, wherein, $$F = \left[\frac{1}{Q}\sum_{k=1}^{Q} Pvalue_s^2(k)\right]^{1/2},$$

wherein, $$Q = \frac{k_{max}}{\langle s \rangle},$$

and <S> represents calculating an average in range S, and with respect to different scale ranges S, $F \propto s^\alpha$, wherein $\propto$ represents a directly proportional or scale relation between two subjects, and $\alpha$ is the scaling index; and obtaining scaling index $\alpha$ in accordance with $F \propto s^\alpha$.

5. The system of claim 4, wherein, said system further comprises an electroencephalogram measuring device configured to measure an electroencephalogram and to transmit the electroencephalogram to the electroencephalogram scaling device.

6. The system of claim 4, wherein, said music analyzing device is configured to implement following steps:

digitizing each music file in the music library to obtain a digital music signal sequence $\{U_i, i=1, 2, \ldots, M\}$, wherein i is the ith time point of said digital music signal sequence, and M is the length of said digital music signal sequence;

obtaining a sequence $\{v_j, j=1, 2, \ldots, M/(presetlength)\}$ by dividing said digital music signal sequence $\{U_i, i=1, 2, \ldots, M\}$ into multiple sub-sequences with a preset length and calculating the standard deviation of each sub-sequence, wherein $v_j$ is the jth data of said sequence $\{v_j, j=1, 2, \ldots, M/(presetlength)\}$;

obtaining an average intensity sequence in accordance with the sequence $\{v_j, j=1, 2, \ldots, M/(presetlength)\}$;

obtaining a fluctuation sequence $\{z_b, b=1, 2, \ldots, M/(presetlength)\}$ which is a one-dimensional random walk sequence in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula, $$z_b = \sum_{j=1}^{b} (v_j)^2 - \langle v^2 \rangle,$$

wherein $$\langle v^2 \rangle = \frac{1}{M/presetlength} \times \sum_{j=1}^{M/presetlength} (v_j)^2;$$

obtaining multiple sub-sequences by shifting a time window with preset width along said fluctuation sequence $\{z_b, b=1, 2, \ldots, M/(presetlength)\}$ with each two neighboring windows exist a fixed overlap length $\tau$;

obtaining a linear trend $\hat{z}_b$ of each sub-sequence by mean of linear regression;

obtaining a detrended fluctuation function $F_D(presetwidth) = \sqrt{\langle(\delta z)^2\rangle}$ in accordance with said sequence $\{z_b, b=1, 2, \ldots, M/(presetlength)\}$ and said linear trend of each sub-sequence, wherein $\delta z = z_b - \hat{z}_b$, and $\langle(\delta z)^2\rangle$ represents calculating the average of $(\delta z)^2$ in the time window; and obtaining said long-range correlation index $\beta$ in accordance with said detrended fluctuation function $F_D(presetwidth)$ by means of following formula:

$$\beta = \frac{d\log F_D(presetwidth)}{d\log(presewidth+3)},$$

wherein, $$\frac{d\log F_D(presetwidth)}{d\log(presewidth+3)}$$

represents the relation between said detrended fluctuation function and the time scaling defined by said preset width of said time window derived from log-log plot.

7. The system of claim 4, wherein, said matching device is configured to implement following steps:

calculating $\gamma$ in accordance with the scaling index $\alpha$ and the long-range correlation index $\beta$, wherein, $\gamma = |\alpha - \beta|$; and if $\gamma$ is within a second given range, the music file with said long-range correlation index $\beta$ is matched with the electroencephalogram with said scaling index $\alpha$.

8. A computer-implemented method for selecting a music file in a music library for relaxing a user, comprising:

obtaining a scaling index $\alpha$ of a measured electroencephalogram of the user;

obtaining a long-range correlation index $\beta$ of each of music files in the music library;

selecting one of the music files, whose long-range correlation index $\beta$ matches the scaling index $\alpha$ of the measured electroencephalogram; and playing, via a music player, the selected music file for the user, wherein said obtaining a scaling index $\alpha$ further comprises:

digitizing said measured electroencephalogram to obtain a discrete-time signal sequence $\{x_i, i=1, 2, \ldots, N\}$, wherein $x_i$ is the ith sampling point of said electroencephalogram and N is the sampling size;

filtering the average amplitude $\langle x \rangle$ from said discrete-time signal sequence $\{x_i, i=1, 2, \ldots, N\}$ to obtain a sequence $\{y_i, i=1, 2, \ldots, N\}$, wherein $y_i$ is defined by the following formula, $$y_i = \sum_{k=1}^{i} (x_k - \langle x \rangle), i = 1 \ldots N,$$

wherein, $$\langle x \rangle = \frac{1}{N}\sum_{i=1}^{N} x_i;$$

applying an Empirical Mode Decomposition (EMD) to said sequence $\{y_i, i=1, 2, \ldots, N\}$ to obtain n intrinsic mode functions and a remainder, wherein n is a positive integer determined by said EMD;

calculating peak-peak intervals in each intrinsic mode function;

merging waveforms between peaks with peak-peak intervals within a first given range S into a new waveform $Pvalue_s(k)$, wherein $10^{(m-1)} \leq s \leq 10^m$, $m=1, 2, \ldots, m_{max}$, and $m_{max}$ is determined by the length N of said sequence $\{y_i, i=1, 2, \ldots, N\}$, and k represents each data point of said merged waveform, wherein $k=1, 2, \ldots, k_{max}$, and $k_{max}$ is determined by the sum of all the peak-peak intervals within the first given range S;

calculating a root mean square of each merged waveform to obtain a wave function F, wherein, $$F = \left[\frac{1}{Q}\sum_{k=1}^{Q} Pvalue_s^2(k)\right]^{1/2},$$

wherein, $$Q = \frac{k_{max}}{\langle s \rangle},$$

and $\langle S \rangle$ represents calculating an average in range S, and with respect to different scale ranges S, $F \propto s^\alpha$, wherein $\propto$ represents a directly proportional or scale relation between two subjects, and $\alpha$ is the scaling index; and obtaining scaling index $\alpha$ in accordance with $F \propto s^\alpha$.

9. The method of claim 8, wherein, said analyzing each music file further comprises:

digitizing each music file in the music library to obtain a digital music signal sequence $\{U_i, i=1, 2, \ldots, M\}$, wherein i is the ith time point of said digital music signal sequence, and M is the length of said digital music signal sequence;

obtaining a sequence $\{v_j, j=1, 2, \ldots, M/(presetlength)\}$ by dividing said digital music signal sequence $\{U_i, i=1, 2, \ldots, M\}$ into multiple sub-sequences with a preset length and calculating the standard deviation of each sub-sequence, wherein $v_j$ is the jth data of said sequence $\{v_j, j=1, 2, \ldots, M/(presetlength)\}$;

obtaining an average intensity sequence in accordance with the sequence $\{v_j, j=1, 2, \ldots, M/(presetlength)\}$;

obtaining a fluctuation sequence $\{z_b, b=1, 2, \ldots, M/(presetlength)\}$ which is a one-dimensional random walk sequence in accordance with the average intensity sequence $\{(v_j)^2, j=1, 2, \ldots, M/(presetlength)\}$, wherein $z_b$ is the bth data of the sequence $\{z_b, b=1, 2, \ldots, M/(presetlength)\}$ which is defined by the following formula, $$z_b = \sum_{j=1}^{b}(v_j)^2 - \langle v^2 \rangle,$$

wherein $$\langle v^2 \rangle = \frac{1}{M/presetlength} \times \sum_{j=1}^{M/presetlength}(v_j)^2;$$

obtaining multiple sub-sequences by shifting a time window with preset width along said fluctuation sequence $\{z_b, b=1, 2, \ldots, M/(presetlength)\}$ with each two neighboring windows exist a fixed overlap length $\tau$;

obtaining a linear trend $\hat{z}_b$ of each sub-sequence by mean of linear regression;

obtaining a detrended fluctuation function $F_D$ (presetwidth)$=\sqrt{\langle(\delta z)^2\rangle}$ in accordance with said sequence $\{z_b, b=1, 2, \ldots, M/(presetlength)\}$ and said linear trend of each sub-sequence, wherein $\delta z = z_b - \hat{z}_b$, and $\langle(\delta z)^2\rangle$ represents calculating the average of $(\delta z)^2$ in the time window; and obtaining said long-range correlation index $\beta$ in accordance with said detrended fluctuation function $F_D$(presetwidth) by means of following formula:

$$\beta = \frac{d\log F_D(presetwidth)}{d\log(presewidth+3)},$$

wherein, $$\frac{d\log F_D(presetwidth)}{d\log(presewidth+3)}$$

represents the relation between said detrended fluctuation function and the time scaling defined by said preset width of said time window derived from log-log plot.

10. The method of claim 9, wherein, said searching out a music file further comprises:

calculating $\gamma$ in accordance with the scaling index $\alpha$ and the long-range correlation index $\beta$, wherein, $\gamma = |\alpha - \beta|$; and if $\gamma$ is within a second given range, the music file with said long-range correlation index $\beta$ is matched with the electroencephalogram with said scaling index $\alpha$.

* * * * *